United States Patent [19]

Middaugh et al.

[11] Patent Number: 5,185,007
[45] Date of Patent: Feb. 9, 1993

[54] SUCTION DRAINAGE INFECTION CONTROL SYSTEM

[75] Inventors: James F. Middaugh, Deerfield; Peter L. Bryant, Lake Forest; Richard W. Grabenkort, Barrington; Timothy J. Oswald, Lincolnshire; Edward S. Tripp, Park City, all of Ill.

[73] Assignee: Abbott Laboratories, Abbott Park, Ill.

[21] Appl. No.: 906,049

[22] Filed: Jun. 26, 1992

Related U.S. Application Data

[63] Continuation of Ser. No. 457,468, Dec. 27, 1989, abandoned, which is a continuation-in-part of Ser. No. 330,552, Mar. 30, 1989, abandoned.

[51] Int. Cl.⁵ .............................................. A61M 1/00
[52] U.S. Cl. .................................... 604/320; 604/321; 604/319; 604/88; 604/91; 604/81; 604/323; 141/65
[58] Field of Search .................... 604/319–321, 604/310–311, 85–89, 317, 318, 322, 323, 83, 84, 91; 137/205; 141/65

[56] References Cited

U.S. PATENT DOCUMENTS

| | | | |
|---|---|---|---|
| 3,32,221 | 4/1967 | Overment | 604/333 X |
| 3,507,282 | 4/1970 | Burding | 604/333 |
| 3,727,788 | 4/1973 | Holbrook | 604/319 X |
| 3,863,634 | 2/1975 | Reynolds et al. | 604/320 X |
| 3,938,540 | 2/1976 | Holbrook et al. | 137/205 |
| 3,982,538 | 9/1976 | Sharpe | 137/197 X |
| 4,116,240 | 9/1978 | Guiney | 604/81 |
| 4,384,580 | 5/1983 | Leviton | 604/319 X |
| 4,505,703 | 3/1985 | Gale et al. | 604/317 |
| 4,529,398 | 7/1985 | Wong et al. | 604/322 X |
| 4,601,704 | 7/1986 | Larkin | 604/87 |
| 4,606,734 | 8/1986 | Larkin et al. | 604/88 X |
| 4,661,100 | 4/1987 | Rechsteiner | 604/317 X |
| 4,681,571 | 7/1987 | Nehring | 137/205 X |
| 4,693,712 | 9/1987 | Bates | 604/323 |
| 4,855,064 | 8/1989 | Schlein | 604/83 X |
| 4,932,937 | 6/1990 | Gustavsson et al. | 604/87 |

FOREIGN PATENT DOCUMENTS

| | | | |
|---|---|---|---|
| 0941700 | 2/1974 | Canada | 604/321 |
| 8700439 | 1/1987 | World Int. Prop. O. | 604/319 |

Primary Examiner—David Isabella
Assistant Examiner—D. Willse
Attorney, Agent, or Firm—Thomas M. Breininger

[57] ABSTRACT

A suction drainage control system wherein waste-treating material is released into a sealed chamber. The chamber comprises of a cover with a flexible liner sealed to and suspended therefrom. A normally closed reservoir is provided on an underside of the cover for storing the waste-treating material therewithin as long as the reservoir remains closed. An externally operated actuator is provided on the cover for opening the reservoir to release the waste-treating material into the sealed chamber.

10 Claims, 5 Drawing Sheets

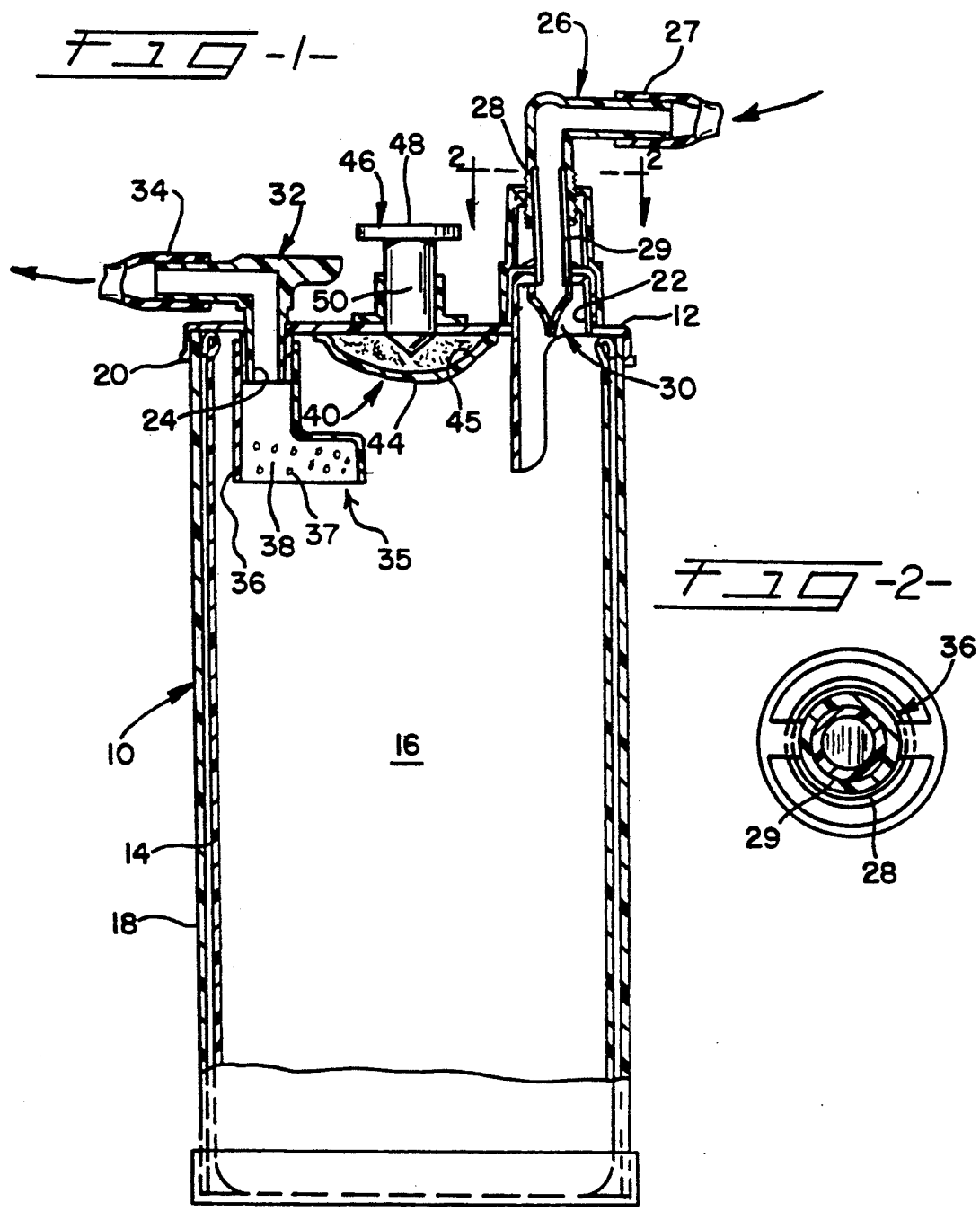

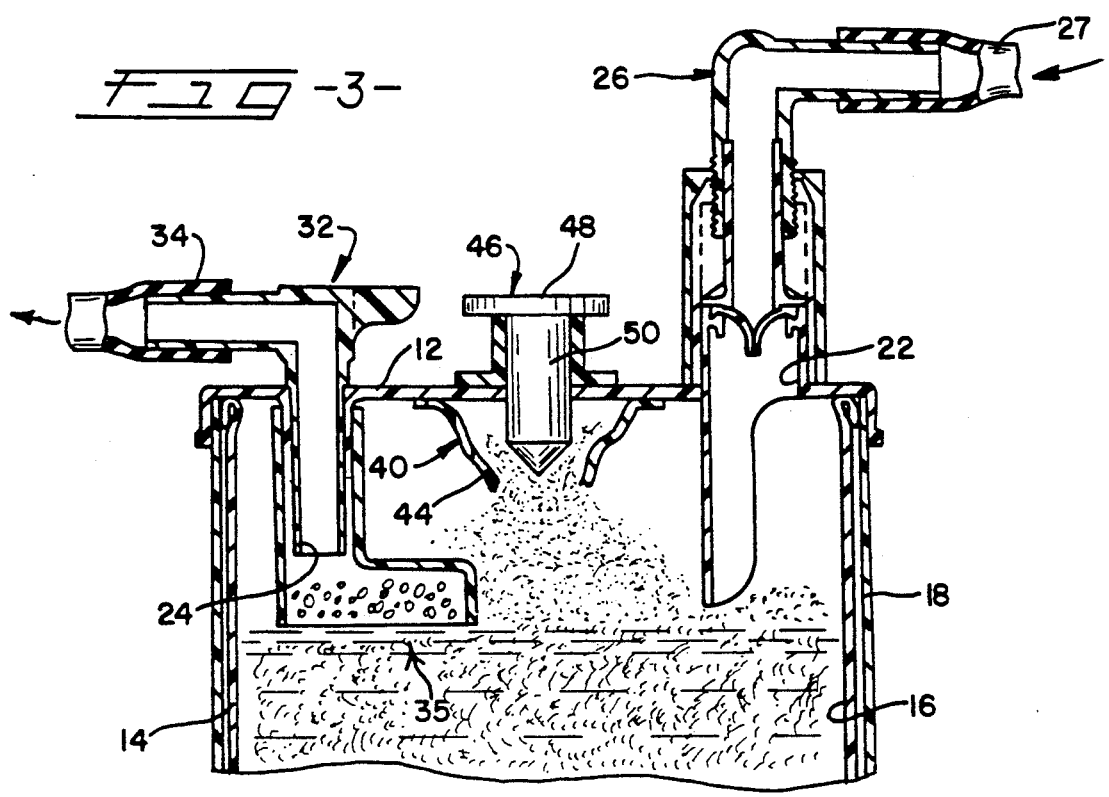
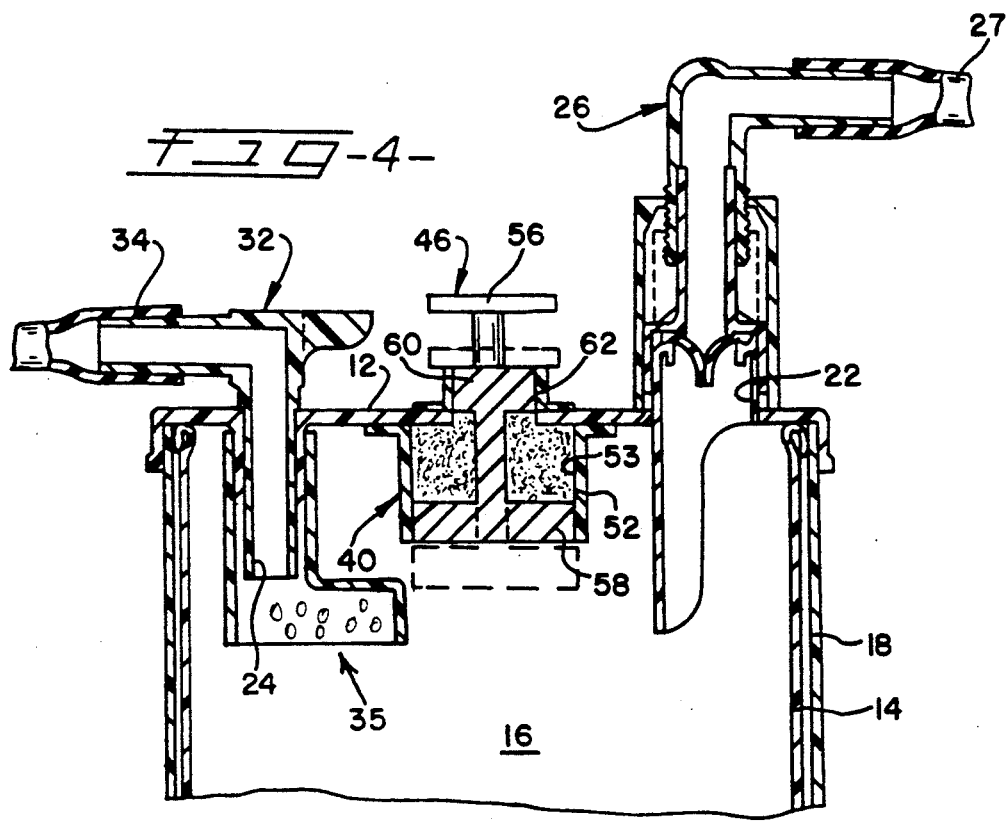

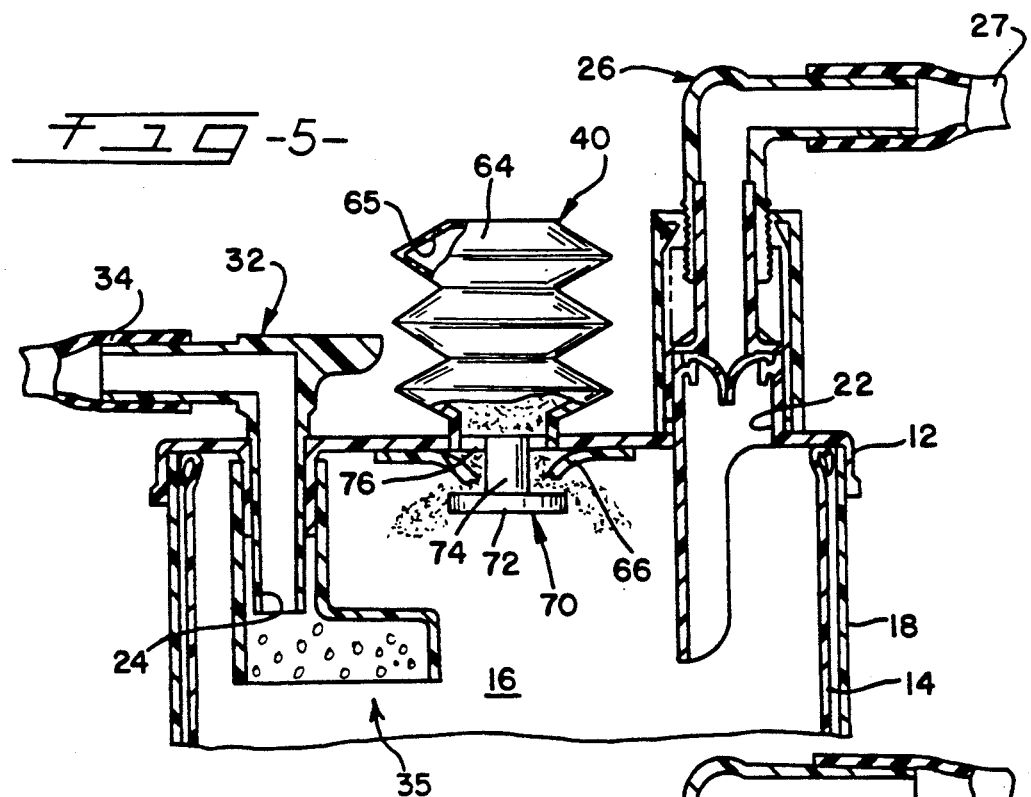
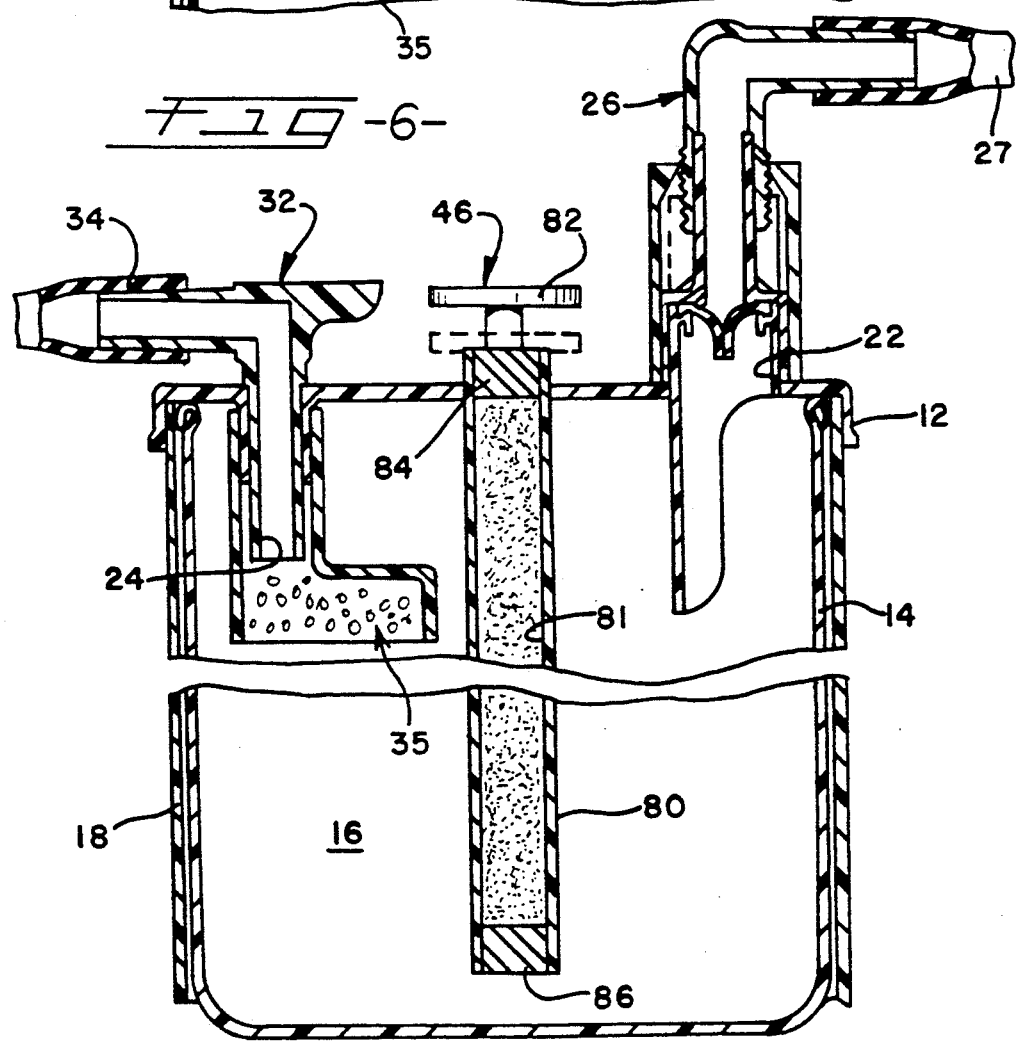

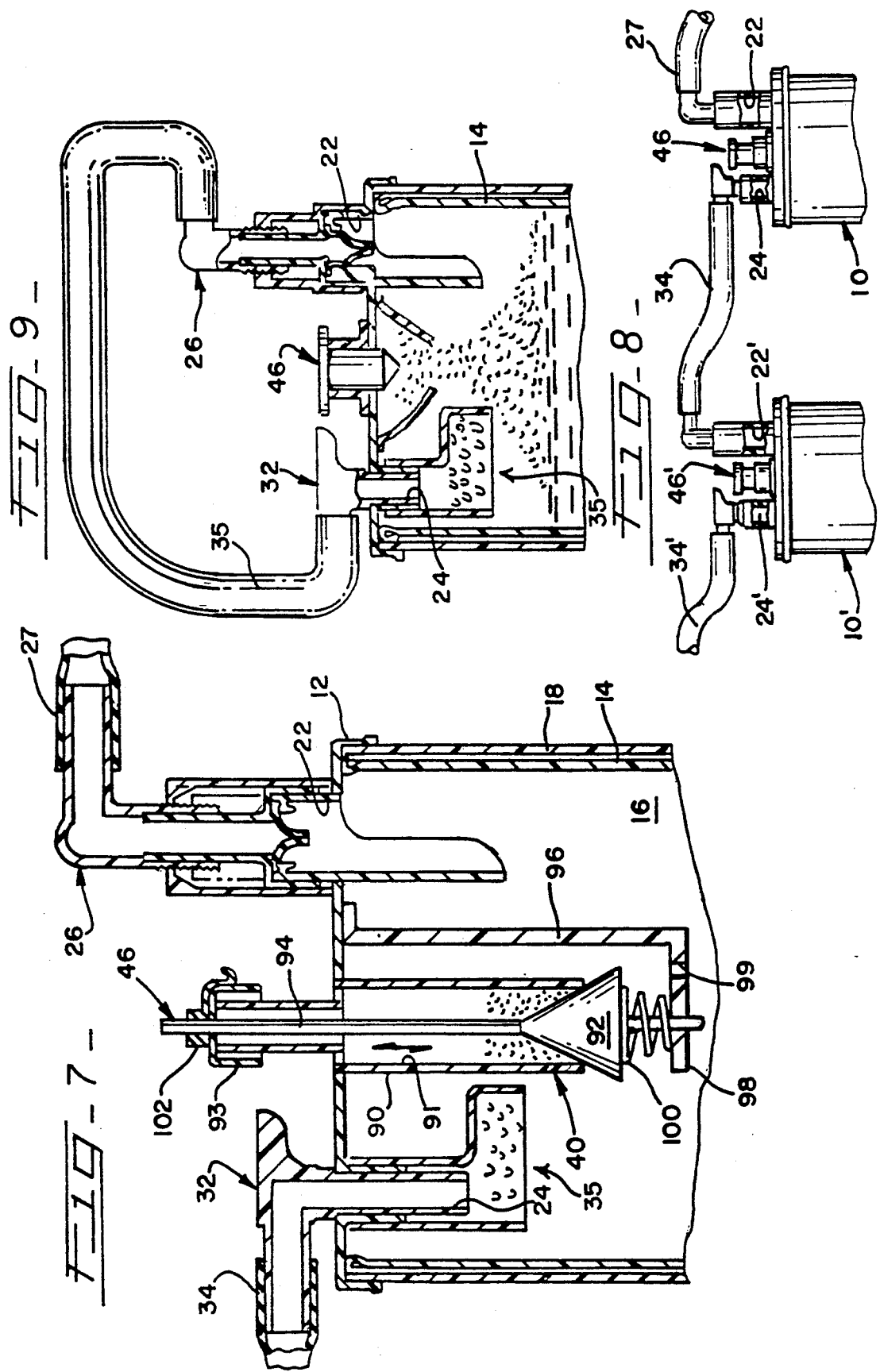

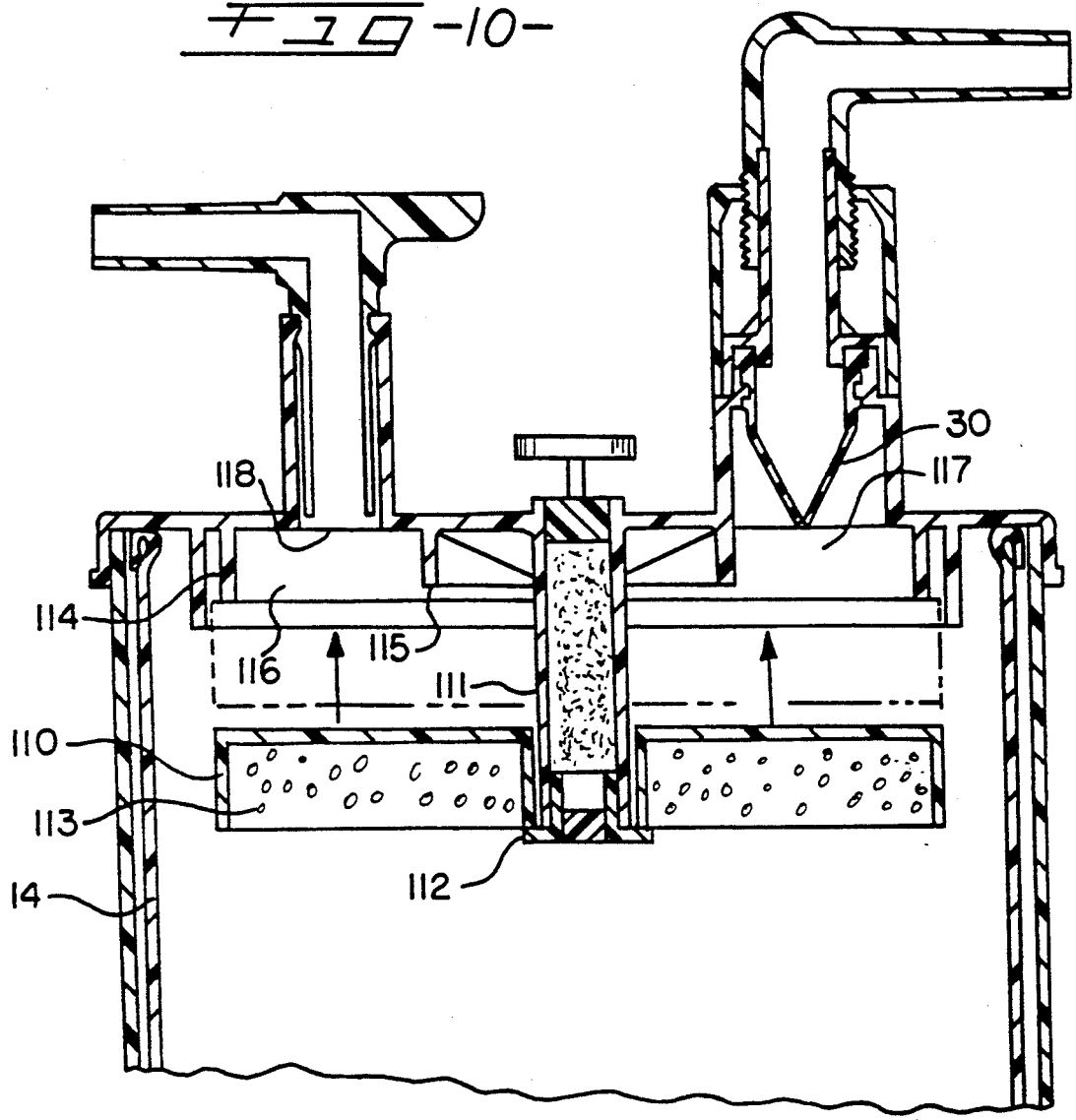

1

SUCTION DRAINAGE INFECTION CONTROL SYSTEM

This application is a continuation of U.S. Pat. application Ser. No. 07/457,468, filed Dec. 27, 1989, now abandoned, which is a continuation-in-part of U.S. Pat. application Ser. No. 07/330,552, filed Mar. 30, 1989, now abandoned.

BACKGROUND OF THE INVENTION

Suction drainage systems having a connection from a rigid container or a flexible liner to the body of a patient and a connection from the container or liner to a suction source have been widely utilized in hospitals. These systems collect waste from surgical and other patients in a disposable container or flexible liner having an integral lid or cover. The waste being collected often is highly infectious and often subject to exposure caused by spills or a failure of the suction drainage system.

Accordingly, it is an object of the present invention to provide a suction drainage container infection control system.

It is a further object of the present invention to provide a suction drainage infection control system incorporating a germicide and/or absorbent in which the germicide and/or absorbent can be introduced into the system by an externally activatable mechanism and/or improved valves and/or a transfer system and/or locking features in the lid to minimize the escape of fluid after capture.

SUMMARY OF THE INVENTION

The present invention is directed to a suction drainage infection control system.

More particularly, the present invention is directed to a suction drainage infection control system wherein a germicide and/or an absorbent (hereinafter referred to as a "waste-treating material") is released or dispensed into a disposable rigid container or flexible liner. The waste-treating material is located in an enclosed reservoir that is included as part of the lid of the rigid container or flexible liner and is released into the container or liner by an externally activated mechanism.

This invention is also directed to a suction drainage infection control system having improved valves, a multi-container transfer system and locking features in the lid of the rigid container or flexible liner.

The suction drainage infection control system of the present invention can include means for chemically treating the waste and/or means for capturing and transferring the waste in a solid or semi-solid state. Each suction drainage canister may be used alone or in series with one or more additional canisters.

The suction drainage infection control system of the present invention minimizes the risk of exposure for hospital personnel to infectious waste by decreasing the risk of infection and spills caused by failure to cap off full or partially full waste containers, accidental cap disconnection and liner breakage.

The suction drainage infection control system of the present invention promotes the safe handling of potentially infectious suction waste by exposing the collected waste to an effective germicidal agent that is capable of killing many types of bacteria and viruses at room temperature. The germicide is effective against HIV, hepatitis B, herpes simplex I, polio, adeno virus, and many other potentially infectious materials, and thus dramatically reduces the potential of cross-contamination between patients and minimizes the associated risk to health care workers.

The suction drainage infection control system of the present invention includes a reservoir that is attached to the cover of the container or liner for storing the waste-treating material therewithin until the reservoir is opened. When the reservoir is opened, the waste-treating material is freely dispersed into the container or liner.

In one form of the invention, the reservoir comprises a rupturable pouch. The rupturable pouch remains sealed to the cover until an externally actuated member is operated to rupture the pouch wall to empty its contents into the interior of the container or liner.

In another form of the invention, the reservoir for storing the waste-treating material includes a walled structure having an open bottom end. A displaceable closure normally closes the open bottom end of the walled structure to contain the waste-treating material therewithin. In response to external activation, the closure is movable relative to the walled structure to allow the waste-treating material to freely fall or disperse from the walled structure into the container or liner.

In still another form of the invention, the reservoir for storing the waste-treating material comprises a collapsible bellows, which is exteriorly mounted on the cover. The collapsible bellows has an open end positioned to empty the waste-treating material into the container or liner. A frangible seal normally closes the open end of the bellows until the exterior portion of the bellows is compressed so that the stored material breaks the seal and empties the waste-treating material into the container or liner.

Other advantages and features of the present invention will become apparent from the following detailed description, the accompanying drawings, and the appended claims.

BRIEF DESCRIPTION OF THE DRAWINGS

FIG. 1 is a vertical cross-sectional illustration of one embodiment of this invention;

FIG. 2 is a sectional view taken along line 2—2 of FIG. 1;

FIG. 3 is a fragmentary vertical sectional view similar to FIG. 1 but illustrating dispersion of waste-treating material into waste contained within a sealed chamber of the present invention;

FIG. 4 is a fragmentary vertical sectional view illustrating a second embodiment of the present invention;

FIG. 5 is a fragmentary vertical sectional view of another embodiment of the present invention;

FIG. 6 is a fragmentary vertical sectional view of still another embodiment of the present invention;

FIG. 7 is a fragmentary vertical sectional view of still another embodiment of the present invention;

FIG. 8 is a fragmentary diagrammatic view of two systems connected in series;

FIG. 9 is a fragmentary view substantially similar to FIG. 3 after the sealed chamber is filled with waste and having the inlet and outlet ports of the sealed chamber closed; and FIG. 10 is a fragmentary vertical sectional view of an embodiment of the present invention that is adapted for use with two or more systems connected in series.

DETAILED DESCRIPTION OF THE PREFERRED EMBODIMENTS

While the present invention is susceptible of embodiment in many forms, there is shown in the drawings and will hereinafter be described several presently preferred embodiments with the understanding that the present specification is to be considered as exemplifications of the invention, which are not intended to limit the invention to the specific embodiments illustrated.

Referring to the drawings, FIG. 1 is a vertical section of a first embodiment of the suction drainage infection control system 10 of the present invention. The system 10 includes a cover 12 and a flexible bag or liner 14. Cover 12 and liner 14 define a sealed chamber 16 in which waste is collected. The system 10 may further include a canister 18 within which the bag 14 is disposed. The cover 12 fits onto the canister 18.

Cover 12 may be formed from a rigid plastic material and is supported by canister 18. As illustrated, liner 14 is suspended from the underside of cover 12. The upper end of liner 14 is fused or sealed to the underside of cover 12 in a completely air tight manner. Preferably, liner 14 is made of substantially transparent rubber-like material or thermoplastic material.

As illustrated, canister 18 surrounds the liner 14 in a protective manner and the skirt portion 20 provided on cover 12 fits over the open end of the canister in air-tight engagement therewith. Canister 18 may be made of relatively rigid plastic material and is closed at its bottom end. Normally, canister 18 itself does not become contaminated by waste which may be highly infectious or even contagious, so it may be repeatedly used without sterilization each time the system 10 is used. In a preferred form, canister 18 has a cylindrical shape although its shape is not critical.

Cover 12 includes an inlet port 22 and an outlet port 24, both of which open to the sealed chamber 16 defined by cover 12 and liner 14. The inlet port 22 is provided with an inlet fitting 26. Fitting 26 directs incoming waste toward the bottom of chamber 16 and is preferably of the type which allows it to be sealed and secured to the cover 12 by a squeezing and/or rotating motion. An upper end of fitting 26 is connected to an inlet tube or line 27 leading from the source to be drained. As illustrated in FIGS. 1 and 2, a lower end 28 of fitting 26 coacts with and is sealed to an upstruck extension 29 of cover 12.

As illustrated in FIG. 1, a valve 30 is provided in series with the inlet port 22. This valve 30 allows for one-way flow of waste from the source to be drained to the sealed liner 14, and in the illustrated embodiment, there is shown a one-way double slit "duck bill" valve which inhibits reverse flow of material through the inlet port 22. Other suitable duck bill valves are disclosed in U.S. Pat. Nos. 3,822,720 and 3,901,272.

Outlet port 24 is likewise provided with an outlet fitting 32, a portion of which projects upwardly from and is sealed to the cover 12. The end of the fitting 32 extending from the cover 12 is connected, as with outlet tube 34, to a negative pressure or vacuum source (not shown) for facilitating operation of the present invention.

A nonmechanical valve 35 is mounted in the lid 12. The nonmechanical valve 35 comprises a housing 36 that contains a polyethylene foam 37 containing swellable moisture-sensitive particles 38 made of polymers or other suitable materials. A suitable nonmechanical valve is disclosed in published PCT Application No. WO 87/00439. This valve permits normal air flow through suction opening 34 until it becomes wet, whereupon the polymer particles swell to block air and waste flow.

The system 10 is further provided with a normally closed reservoir, generally indicated by reference numeral 40, which is externally activated to release waste-treating material into the sealed chamber 16 of the system 10. As long as the reservoir 40 remains closed, a predetermined volume of waste-treating material is contained therewithin. The ability to externally control the release of the waste-treating material reduces operator exposure to the waste within chamber 16.

When the reservoir 40 is opened, the waste-treating material is dispensed into the sealed chamber 16. As used herein, the terms "dispensed" or "dispersion" are meant to include the release of waste-treating material into the sealed chamber 16. The waste-treating material may be in the form of a powder or liquid (single or multi-component) disinfectant and preferably comprises a germicide and/or an absorbent. The germicide and/or absorbent will treat contaminants contained in the waste. In a preferred embodiment, the absorbent is of a type that will swell in size upon dispersion into the waste material in the sealed chamber.

Representative suitable germicides include calcium hypochlorite, chlorinated trisodium phosphate, N-chlorosuccinimide, 1,3-dichloro-5,5-dimethylhydantoin, potassium dichloro-s-triazinetrione, sodium benzenesulfonchloramide, sodium hypochlorite, sodium p-toluenesulfonchloramide, sodium dichloroisocyanurate, dihydrate, sodium dichloro-s-triazinetrione, p-sulfondichlor-amidobenzoic acid, p-toluenesulfondichloramide, trichloroisocyanuric acid, trichloromelamine, alcohols, fomaldehyde, glutaraldehyde, hydrogen peroxide, iodine, quaternary ammonium compounds, paraacetic acid, paraformaldehyde, and phenols. Preferred germicides include 1,3-dichloro-5,5-dimethylhydantoin, potassium dichloro-s-triazinetrione, N-chlorosuccinimide, and sodium dichloroisocyanurate dihydrate.

Representative suitable absorbents include cellulose fibers, cross-linked polymeric salts, diatomaceous earth, dried clay, expanded silicate particulates, ground corncobs, perlite, silica gel, shredded polypropylene microfibers, sodium/calcium borosilicate glass, starch grafted sodium polyacrylate, thermally reticulated polyether polyurethane, and vermiculite.

In the embodiment illustrated in FIG. 1, the reservoir 40 is a rupturable pouch 44. As illustrated, the pouch 44 is glued, sealed or otherwise secured about its peripheral edge to the underside of cover 12. The pouch 44 defines a cavity 45 which contains and isolates the waste-treating material therewithin from the contents of the sealed chamber 16. Pouch 44 is preferably formed from an aluminum foil, plastic, or paper, or combinations thereof, having a thickness of about several mils.

As shown in FIG. 3, to release the waste-treating material from the pouch 44, a plunger-like actuator 46 is displaceably mounted on and in sealing relationship with cover 12 above pouch 44. At least a portion of the actuator 46 extends outside cover 12. As illustrated, the actuator 46 defines a cap portion 48 providing for quick and selective ·-tuation of the actuator by an operator. A stem portion 50 of the actuator 46 depends from the cap portion 48. Stem portion 50 extends through the cover 12 and is in sealing relationship thereto. The actuator 46, while tightly fitted in cover 12, is operatively movable between first and second positions without degrading the integrity of the chamber 16.

A second embodiment of a system is illustrated in FIG. 4. The system illustrated in FIG. 4 is substantially similar to that discussed in detail above and therefore those parts comprising the system of the second embodiment which function similarly to those parts discussed above will be identified with like reference numerals and will not be further discussed.

In the second embodiment, the reservoir 40 wherein the waste-treating material is enclosed and releasably stored is defined by a rigid cylindrical structure 52 defining a cavity 53. Structure 52 may be formed from glass, plastic, paper, or the like, and has walls which are sealed to and depend from the underside of cover 12 and define an open-bottom end for structure 52. As will be appreciated, the cylindrical shape of structure 52 is preferred but is not critical to the structure.

An externally activated, plunger-like actuator 46 is displaceably mounted on the cover 12 for normally closing the open-bottom end of structure 52. Actuator 46 is movable between first and second positions and is in sealing relationship with the cover 12 such as by a press-fit to inhibit waste material from inadvertently escaping from the system 10. The actuator 46 in FIG. 4 includes a cap portion 56 which extends outside of cover 12 at its upper end. A cylindrically-shaped plug portion 58 is provided at the lower end of the actuator. Intermediate its ends, the actuator 46, illustrated in FIG. 4, is provided with a cylindrical spool portion 60 defining an axially elongated land 62.

The actuator 46, illustrated in FIG. 4, is externally operated to effect release of the waste-treating material from the normally closed structure 52. As illustrated, plug portion 58 of the actuator 46 is connected to cap portion 56 and is snugly received within the open bottom end of the walled structure 52 to contain the waste-treating material within the reservoir 40 until the actuator 46 is externally activated.

A third embodiment of a system is illustrated in FIG. 5. The system illustrated in FIG. 5 is comprised of many of the same components as the system illustrated in FIG. 1. Accordingly, those component parts illustrated in FIG. 5, which perform in substantially the same manner as those in FIG. 1 have been identified with like reference numerals.

In this embodiment, reservoir 40 is formed by a hollow, collapsible bellows 64 that defines a cavity 65 wherein the waste-treating material is contained. Bellows 64 is provided with an open-bottom end which is sealed to the cover 12. As illustrated in FIG. 5, bellows 64 extends upwardly from cover 12 such that it may be externally activated. Bellows 64 preferably locks in a collapsed position to indicate activation of the system.

As illustrated in FIG. 5, a frangible seal or diaphragm 66 is provided beneath the open end of the bellows 64 and is sealed to the underside of the cover 12. The frangible seal 66 normally maintains the waste-treating material within the bellows 64 until the bellows is externally operated to effect release of the waste-treating material into the sealed chamber 16.

As further illustrated in FIG. 5, means 70 for spreading the waste-treating material as it is dispersed into the sealed chamber 16 may be provided in combination with the bellows 64. As illustrated, means 70 may include a circular plate-like member 72 arranged in spaced relation beneath the lower end of bellows 64 and beneath the seal 66. Member 72 is disposed such that the waste-treating material dispensed from the bellows 64 strikes the member 72 in a manner imparting a spreading effect thereto as the waste-treating material freely falls into the sealed chamber 16. A stem-like projection 74 connects member 72 to the open end of the bellows 64 as through radial spokes 76 or other suitable connection means.

Another embodiment of the present invention is illustrated in FIG. 6. The system illustrated in FIG. 6 is comprised of many of the same components as the system illustrated in FIG. 1. Accordingly, those component parts which function similarly to those illustrated in FIG. 1 have been identified by like reference numerals in FIG. 6.

In the embodiment illustrated in FIG. 6, reservoir 40 is defined by an elongated tube 80 which depends from and has its upper end suitably sealed to cover 12. Tube 80 is preferably comprised of a flexible plastic material and defines a cavity 81 which is open at its upper and lower ends. The lower end of reservoir 40 is normally closed with a plug 86. As will be understood, the flexibility of tube 80 allows it to be configured in arrangements other than that illustrated in FIG. 6. For example, that portion of tube 80 which depends from cover 12 could be arranged in a generally U-shaped configuration or a generally S-shaped configuration depending upon the particular size of the sealed chamber within which tube 80 is accommodated. Alternatively, tube 80 could be formed from an appropriately configured rigid-tubular material.

An externally activated plunger-like actuator 46 controls the release of the waste-treating material from the reservoir 40 illustrated in FIG. 6. Actuator 46 is movable relative to the cover 12 between first and second positions. In either of its two positions, the actuator 46 is in sealing relationship with the open end of tube 80 to inhibit waste from inadvertently escaping therefrom. As illustrated, actuator 46 includes a cap portion 82 at its upper end and a piston portion 84 at its lower end which is joined to the cap portion 82. As illustrated, at least a portion of the cap portion 82 is arranged outside of the cover 12 to permit release of waste-treating material from the reservoir 40 through external operation of the actuator 46. The piston portion 84 of actuator 46 is slidably received within the tube 80 and serves to seal the upper end of the tube regardless of the position of actuator 46.

Plug 86 is snugly received within the lower end of tube 80. Preferably, plug 86 is formed of a low density material such as cork or a rubber material with buoyant properties. Plug 86 will float to the top of the waste material and indicate that the waste-treating material has been emptied into the sealed chamber. The depression of the actuator 46 results in compression of the waste-treating material contained within tube 80 and, ultimately, release of plug 86 from the bottom end of the tube 80. Once plug 86 is removed from the bottom end of tube 80, the waste-treating material freely falls into the sealed chamber 16.

Still another embodiment of a system is illustrated in FIG. 7. The system illustrated in FIG. 7 is comprised of many of the same components as the system illustrated in FIG. 1. Accordingly, those parts which function in a substantially similar manner to those illustrated in FIG. 1, will be identified with like reference numerals.

In the embodiment illustrated in FIG. 7, reservoir 40 is defined by an elongated cylindrical tube 90 which passes through cover 12 and defines a cavity 91. That portion of tube 90 extending into the sealed chamber 16 is preferably comprised of a flexible material which is sealed to cover 12 and is provided with open upper and lower ends. The upper end of tube 90 is suitably sealed to and upwardly extends from cover 12.

As in the other embodiments, an externally activated plunger-like actuator 46 selectively controls dispersion of the waste-treating material into the sealed chamber 16. As illustrated in FIG. 7, actuator 46 of this embodiment includes a resiliently biased conically shaped plunger 92 arranged at the open-bottom end of tube 90 for selective movement between first (open) and second (closed) positions. Plunger 98 is secured to an endwise movable plunger rod or guide 94. In its preferred form, plunger 92 and rod 94 are formed from the same material, i.e., a rigid or semi-rigid plastic with buoyant properties. Plunger 92 and rod 94 could be formed from different materials.

A generally L-shaped bracket 96 depends from the underside of cover 12 and is supported adjacent the plunger rod 94 such that a lowermost leg 98 of bracket 96 extends beneath plunger 92. Leg 98 is provided with suitably shaped apertures or slots 99 permitting waste-treating material to pass therethrough. A resilient member or spring 10? is disposed between leg 98 and the underside of the plunger 92. The spring 100 could be either a separate item or could be formed integrally with the bracket 96.

As illustrated, the plunger rod 94 is guided at its upper and lower ends. At its upper end, tube 90 is provided with an apertured guide 93 through which plunger rod 94 extends. At its lower end, plunger rod 42 is guided by leg 98. An apertured sealing member 102 is also provided at the upper end of tube 90 to inhibit inadvertent escape of waste-treating material and operates to hold the plunger rod 94 in place. The plunger rod 94 is operated outside cover 12.

As illustrated in FIG. 8, two systems 10 and 10' can be arranged in series relative to each other between the suction source and the source from which waste is to be drawn. In such arrangement, the outlet tube 34' of system 10' is connected to a source of suction or negative pressure. The outlet tube 34 extending from outlet port 24 of system 10 is connected to inlet port 22' of system 10'. The inlet port 22 of system 10 extends, via inlet tube 27, to the source of waste.

FIG. 10 is a fragmentary vertical section of an embodiment of the present invention that is adapted for use with two or more canisters connected in series as shown in FIG. 8. In this embodiment, a float 110 is slidably mounted on post 111, which has a knob 112 at its lowermost portion to support the float in its lowermost position. The float 110 is packed with buoyant material 113 so that when the waste reaches a level in the liner 14 where it contacts the lower surface of the buoyant material 113 the float 110 rises until circular wall 114 is contacted by the upper surface of the float 110. Circular wall 114 forms with circular wall 115, an annular channel 116 through which opening 117 communicates with opening 118. The float 110 thus prevents the flow of waste into the liner 14. However, as seen from the drawings, suction is present and continues to draw in waste through valve 30. As a result of the suction, the waste will flow directly from inlet opening 117 to outlet opening 118 through circular channel 116. As shown in FIG. 8, waste then can pass from one canister to another. This feature is referred to as the transfer system.

When the system of the present invention is idle or before the suction source is connected to the system, reservoir 40 will be in a normally closed position. Because at least a portion of the actuator 46 extends exteriorly of the cover 12, the raised position of the actuator 46 provides a visual indication that the waste-treating material contained within the capsule 40 has not yet been dispensed or released into the sealed chamber 16.

This invention is extremely simple in operation. During operation, negative pressure or suction is introduced into the sealed chamber 16 as by connecting the outlet tube 34 leading from the suction source to the outlet port 24. When suction or negative pressure is created in the sealed chamber 16, a positive pressure differential is developed on opposite sides of valve 30. Waste drawn through the inlet port 22, which is suctioned from a source (not shown), forces an expansion of the valve 30 to permit flow therethrough into the sealed chamber 16 wherein the waste is received and collected. The positive pressure differential allows the valve 30 to serve as a one-way flow valve which inhibits reverse flow toward the source from which the waste is drawn.

Release of the waste-treating material from the normally closed reservoir 40 into the sealed chamber 16 is effected at any time but preferably happens just prior to or during the collection of contaminated waste in the sealed chamber 16. External control of the actuator 46 to release the waste-treating material also provides a visual indication that the waste-treating material has been dispensed or released into the sealed chamber 16.

Although the various embodiments illustrated herein are directed to a suction drainage infection control system having a flexible liner, the present invention is equally applicable to a rigid container containing germicide and/or absorbent agents which mix with and reduce the risk to infectious control waste. Thus, as used herein, the term "waste receptacle" is intended to include both disposable rigid containers and canisters having disposable, flexible liners.

From the foregoing, it will be apparent that numerous modifications and variations can be effected without departing from the true spirit and scope of the novel concept of the present invention. It will be appreciated that the present disclosure is intended to set forth exemplifications of the invention which are not intended to limit the invention to the specific embodiments illustrated. The disclosure is intended to cover by the appended claims all such modifications as fall within the scope of the claims.

What is claimed is:

1. A suction system for draining waste from a source, said suction system comprising:
    a sealed chamber that includes a flexible liner which is sealed at its upper end to a flat rigid cover, said cover including inlet and outlet means;
    a normally closed reservoir carried by said cover for storing a predetermined amount of waste-treating material therewithin; and
    an externally operated actuator provided on said cover for controlling release of waste-treating material from said reservoir means into said sealed chamber.

2. A suction system as in claim 1 wherein a nonmechanical val' prevents suction from being applied when the valve is contacted by waste.

3. A suction system as in claim 2 wherein the nonmechanical valve contains fluid swellable particles.

4. A suction system as in claim 1 wherein said reservoir comprises a collapsible bellows exteriorly positioned on said cover, said bellows having an open end positioned to release waste-treating material contained in said bellows into said sealed chamber, and frangible seal means for closing the open end of aid bellows until said bellow is collapsed.

5. A suction system as in claim 4 further including means disposed beneath the open end of said bellows for dispersing the waste-treating material as it is released into the sealed chamber.

6. A suction system as in claim 1 wherein said inlet means is provided with valve means for limiting flow of waste from said sealed chamber.

7. A suction system as in claim 1 wherein said reservoir includes a rupturable pouch sealed to an underside of said cover.

8. A suction system as in claim 7 wherein said actuator is displaceably mounted on said cover for effecting rupture of said pouch to effect release of said waste-treating material into said sealed chamber.

9. A suction system as in claim 1 wherein said reservoir includes an elongated tube sealed to and depending from said cover, said tube having an open bottom end which is normally closed by said actuator.

10. A suction system as in claim 9 wherein said actuator includes a resiliently biased plunger arranged at the open bottom end of said elongated tube for normally inhibiting the free flow of waste-treating material from said reservoir.

* * * * *